US00PP27210P2

(12) United States Plant Patent
Bullis

(10) Patent No.: US PP27,210 P2
(45) Date of Patent: Sep. 27, 2016

(54) ***NEOREGELIA* PLANT NAMED 'MONA LISA'**

(50) Latin Name: *Neoregelia carolinae×Neoregelia×hybrida*
Varietal Denomination: Mona Lisa

(71) Applicant: Patricia Gomez Bullis, Princeton, FL (US)

(72) Inventor: Patricia Gomez Bullis, Princeton, FL (US)

(73) Assignee: Bullis Bromeliads, Princeton, FL (US)

( * ) Notice: Subject to any disclaimer, the term of this patent is extended or adjusted under 35 U.S.C. 154(b) by 93 days.

(21) Appl. No.: 14/544,216

(22) Filed: Dec. 9, 2014

(51) Int. Cl.
*A01H 5/02* (2006.01)

(52) U.S. Cl.
USPC ..... Plt./370

(58) Field of Classification Search
USPC ..... Plt./370
See application file for complete search history.

*Primary Examiner* — Annette Para
(74) *Attorney, Agent, or Firm* — C. A. Whealy

(57) ABSTRACT

A new and distinct cultivar of *Neoregelia* plant named 'Mona Lisa', characterized by its upright and outwardly arching growth habit; leaves that are dark green in color with cream-colored stripes and dark-green margins; upper leaves, proximally, rosy red in color; and good interiorscape and landscape performance.

1 Drawing Sheet

Botanical designation: *Neoregelia carolinae×Neoregelia×hybrida.*

Cultivar denomination: 'MONA LISA'.

BACKGROUND OF THE INVENTION

The present invention relates to a new and distinct cultivar of *Neoregelia* plant, botanically known as *Neoregelia carolinae×Neoregelia×hybrida*, and hereinafter referred to by the name 'Mona Lisa'.

The new *Neoregelia* plant is a product of a planned breeding program conducted by the Inventor in Princeton, Fla. The objective of the breeding program is to create new *Neoregelia* plants with uniquely colored leaves.

The new *Neoregelia* plant originated from a cross-pollination made by the Inventor in 2002 in Princeton, Fla. of an unnamed proprietary selection of *Neoregelia carolinae*, not patented, as the female, or seed, parent with *Neoregelia×hybrida* 'Passion', not patented, as the male, or pollen, parent. The new *Neoregelia* plant was discovered and selected by the Inventor as a single plant within the progeny of the stated cross-pollination in a controlled greenhouse environment in Princeton, Fla. in 2003.

Asexual reproduction of the new *Neoregelia* plant by offsets in a controlled environment in Princeton, Fla. since 2003, has shown that the unique features of this new *Neoregelia* plant are stable and reproduced true to type in successive generations.

SUMMARY OF THE INVENTION

Plants of the new *Neoregelia* have not been observed under all possible combinations of environmental conditions and cultural practices. The phenotype may vary somewhat with variations in environment conditions such as temperature and light intensity without, however, any variance in genotype.

The following traits have been repeatedly observed and are determined to be the unique characteristics of 'Mona Lisa'. These characteristics in combination distinguish 'Mona Lisa' as a new and distinct *Neoregelia* plant:

1. Upright and outwardly arching growth habit.
2. Leaves that are dark green in color with cream-colored stripes and dark-green margins; upper leaves, proximally, rosy red in color.
3. Good interiorscape and landscape performance.

Plants of the new *Neoregelia* differ primarily from plants of the female parent selection in the following characteristics:

1. Leaf coloration of plants of the new *Neoregelia* is more stable than leaf coloration of plants of the female parent selection.
2. Plants of the new *Neoregelia* and the female parent selection differ in leaf color as plants of the female parent selection have orange-colored leaves.

Plants of the new *Neoregelia* differ primarily from plants of the male parent, 'Passion', in the following characteristics:

1. Plants of the new *Neoregelia* have shorter leaves than plants of 'Passion'.
2. Plants of the new *Neoregelia* and 'Passion' differ in leaf color as plants of 'Passion' have green-colored leaves.

Plants of the new *Neoregelia* can be compared to plants of the *Neoregelia* 'Raphael', disclosed in U.S. Plant Pat. No. 10,719. In side-by-side comparisons conducted in Princeton, Fla., plants of the new *Neoregelia* and 'Raphael' differed primarily in the following characteristics:

1. Plants of the new *Neoregelia* were more compact than plants of 'Raphael'.
2. Plants of the new *Neoregelia* and 'Raphael' differed in leaf color.

BRIEF DESCRIPTION OF THE PHOTOGRAPHS

The accompanying colored photographs illustrate the overall appearance of the new *Neoregelia* plant showing the colors as true as it is reasonably possible to obtain in colored reproductions of this type. Colors in the photographs may differ slightly from the color values cited in the detailed botanical description which accurately describe the colors of the new *Neoregelia* plant.

The photograph at the bottom of the sheet is a side perspective view of a typical flowering plant of 'Mona Lisa' grown in a container.

The photograph at the top of the sheet is a top perspective view of a typical flowering plant of 'Mona Lisa'.

DETAILED BOTANICAL DESCRIPTION

The aforementioned photographs and following observations, measurements and values describe flowering plants grown during the spring and summer in 15-cm containers in a polypropylene-covered greenhouse in Princeton, Fla. and under cultural practices typical of commercial *Neoregelia* production. During the production of the plants, day temperatures ranged from 28° C. to 30° C., night temperatures ranged from 18° C. to 22° C. and light levels averaged 3,200 foot-candles. Plants were 13 months old when the photographs and description were taken. In the following description, color references are made to The Royal Horticultural Society Colour Chart, 2007 Edition, except where general terms of ordinary dictionary significance are used.

Botanical classification: *Neoregelia carolinae*×*Neoregelia*× *hybrida* 'Mona Lisa'.

Parentage:

*Female, or seed, parent*.—Unnamed proprietary selection of *Neoregelia carolinae*, not patented.

*Male, or pollen, parent*.—*Neoregelia*×*hybrida* 'Passion', not patented.

Propagation:

*Type*.—By offsets.

*Time to initiate roots, summer*.—About 30 to 40 days at temperatures about 28° C. to 30° C.

*Time to initiate roots, winter*.—About 45 to 55 days at temperatures about 28° C. to 30° C.

*Time to produce a rooted young plant, summer*.—About three months at temperatures about 28° C. to 30° C.

*Time to produce a rooted young plant, winter*.—About four months at temperatures about 18° C. to 22° C.

*Root description*.—Medium in thickness, fibrous; yellow to beige tan in color.

*Rooting habit*.—Moderately freely branching; medium density.

Plant description:

*Plant and growth habit*.—Upright and outwardly arching growth habit; rosette leaves are erect when young, becoming outwardly arching with development; plants readily produce uniform offsets; vigorous growth habit.

*Plant height*.—About 17.6 cm.

*Plant diameter or spread*.—About 62 cm.

*Internode length*.—About 4 mm.

*Stem texture*.—Smooth, glabrous.

*Stem color*.—Close to 155B.

Leaf description:

*Arrangement*.—Rosette, spiral phyllotaxis; simple; sessile, clasping.

*Shape*.—Oblong with broad sheathing base.

*Apex*.—Cuspidate.

*Base*.—Truncate.

*Margin*.—Serrate, spinose.

*Length*.—About 36.5 cm.

*Width, mid-section*.—About 6.3 cm.

*Width, base*.—About 9.6 cm.

*Texture, upper and lower surfaces*.—Smooth, glabrous; leathery; longitudinally ribbed.

*Luster, upper and lower surfaces*.—Glossy, shiny.

*Venation pattern*.—Parallel.

*Color*.—Lower leaves, upper surface: Centers, close to N137A; margins, close to 160D; venation, close to N137A and 160D. Lower leaves, lower surface: Centers, close to N137A to N137B; margins, close to 160D; venation, close to N137A and 160D. Upper leaves, upper surface: Centers, close to N137A; longitudinal stripes, close to 137C; margins, close to 160D; venation, close to N137A and 160D; uppermost leaves, close to 53A. Upper leaves, lower surface: Centers, close to N137A; margins, close to 160D; venation, close to N137A and 160D.

Inflorescence description:

*Inflorescence form*.—Terminal flat-topped compact corymb located inside the leaf rosette; about 138 flowers develop per inflorescence.

*Time to flower*.—Plants begin flowering about eight to ten weeks after planting; plants flower naturally during the spring in Florida.

*Flower longevity*.—Individual flowers last about one to two days on the plant; flowers persistent.

*Fragrance*.—None detected.

*Inflorescence length*.—About 5.8 cm.

*Inflorescence diameter*.—About 4.8 cm.

*Flower size*.—Length: About 5 cm. Diameter: About 6 mm.

*Flower buds*.—Length: About 3.5 cm. Diameter: About 6 mm. Shape: Narrowly elongate. Color: Close to 94D.

*Petals*.—Quantity per flower: Three in a single whorl. Shape: Oblanceolate. Apex: Acute. Base: Truncate. Margin: Entire. Length: About 3.7 cm. Width: About 6 mm. Texture, upper and lower surfaces: Smooth, glabrous. Color: When opening, upper (inner) surface: Close to 93B to 93C. When opening, lower (outer) surface: Close to 92C to 92D. Fully opened, upper (inner) surface: Close to 93B, 93C and 93D; towards the base, close to NN155D. Fully opened, lower (outer) surface: Close to 92C; towards the base, close to NN155D.

*Flower bracts*.—Quantity per flower: One. Shape: Elliptical. Length: About 3.5 cm. Width: About 1.2 cm. Texture, upper and lower surfaces: Membraneous. Color, upper and lower surfaces: Close to 145D.

*Sepals*.—Quantity per flower: Three in a single whorl. Shape: Oblanceolate. Apex: Acuminate. Base: Truncate. Margin: Entire. Length: About 2.3 cm. Width: About 7 mm. Texture, upper and lower surfaces: Smooth, glabrous. Luster, upper and lower surfaces: Glossy, shiny. Color, upper surface: Close to 146D; towards the base, close to 145D. Color, lower surface: Close to 146C to 146D.

*Peduncles*.—Length: About 7 mm. Diameter: About 1.4 cm. Strength: Strong. Aspect: Typically erect. Texture: Smooth, glabrous. Color: Close to 155A.

*Pedicels*.—Length: About 1.1 cm. Diameter: About 4 mm. Strength: Strong. Aspect: Typically erect to outward and curving upright. Texture: Smooth, glabrous. Color: Close to 155B.

*Stamens*.—Quantity per flower: Six. Filament length: About 1.7 cm; partially adnate to the petals. Filament color: Close to NN155D. Anther shape: Lanceolate. Anther length: About 4 mm. Anther color: Close to 158C. Pollen amount: Scarce. Pollen color: Close to 158C.

*Pistils*.—Quantity per flower: One. Pistil length: About 3.7 cm. Stigma shape: Oval, elongated. Stigma color: Close to NN155B. Style length: About 1.5 cm. Style color: Close to NN155D. Ovary color: Close to NN155D.

*Fruits and seeds*.—To date, fruit and seed production have not been observed on plants of the new *Neoregelia*.

Temperature tolerance: Plants of the new *Neoregelia* have been observed to tolerate temperatures ranging from about 2° C. to about 37° C.

Interior & garden performance: Plants of the new *Neoregelia* have been observed to have good postproduction longevity under interior conditions and to have good garden performance. Plants of the new *Neoregelia* have been observed to tolerate summer rains.

Pathogen & pest tolerance/resistance: Plants of the new *Neoregelia* have been observed to be somewhat tolerant to root rot pathogens such as *Pythium* and *Phytophthora*. Tolerance and resistance to pests and other pathogens common to *Neoregelia* plants has not been observed.

It is claimed:

1. A new and distinct *Neoregelia* plant named 'Mona Lisa' as illustrated and described.

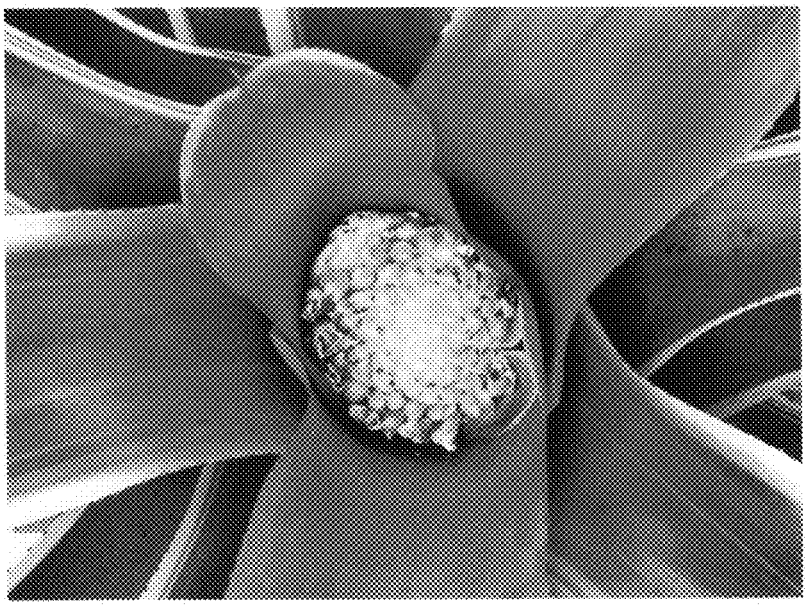
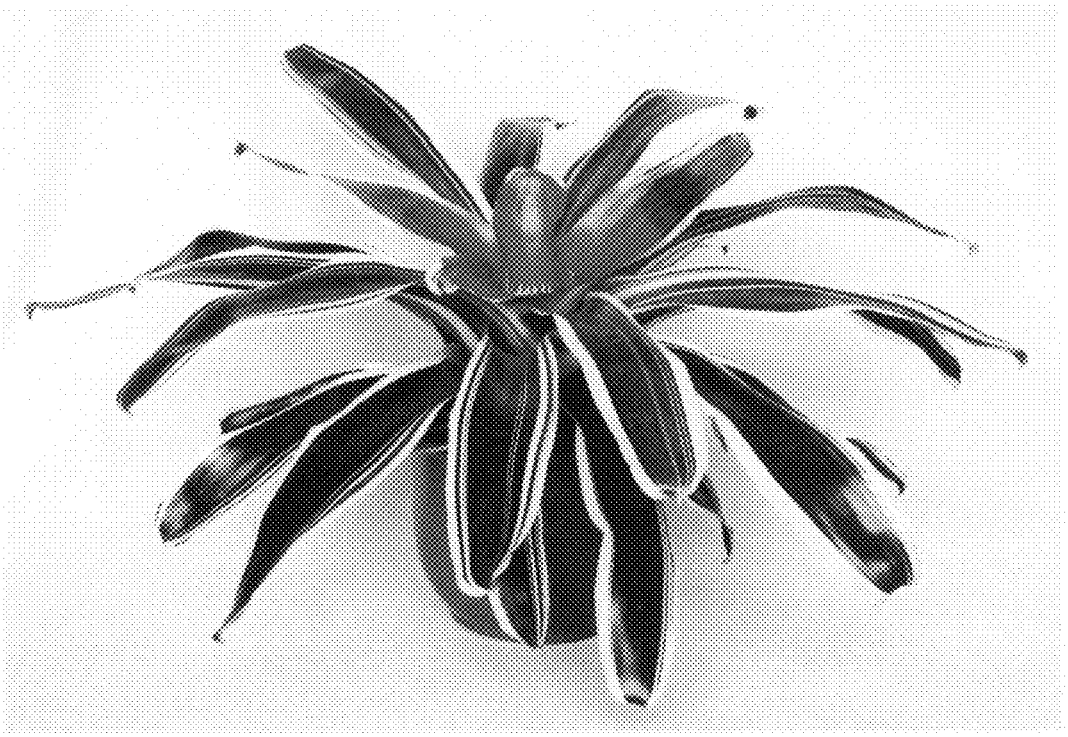

* * * * *